Figure 1:
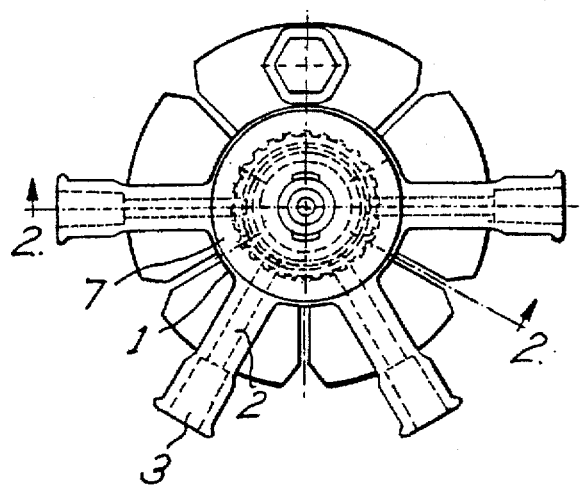

United States Patent
Haindl

[11] Patent Number: 5,695,478
[45] Date of Patent: Dec. 9, 1997

[54] SAFETY CONNECTOR FOR INFUSION THERAPY

[76] Inventor: Hans Haindl, Hauptstrasse 39, 30974 Wennigsen, Germany

[21] Appl. No.: 403,915

[22] PCT Filed: Jul. 31, 1993

[86] PCT No.: PCT/EP93/02049

§ 371 Date: Mar. 16, 1995

§ 102(e) Date: Mar. 16, 1995

[87] PCT Pub. No.: WO94/06489

PCT Pub. Date: Mar. 31, 1994

[30] Foreign Application Priority Data

Sep. 18, 1992 [DE] Germany .......... 42 31 276.0

[51] Int. Cl.⁶ ............................ A61M 5/00
[52] U.S. Cl. .......... 604/247; 604/30; 604/256; 604/258; 128/DIG. 12; 137/606; 137/860
[58] Field of Search .......... 137/71, 625, 625.4, 137/625.44, 625.45, 852, 855, 527, 527.8, 860, 137, 606; 604/30, 32, 34, 80–83, 89–91, 283, 246, 247, 248, 255, 257, 258; 128/DIG. 12

[56] References Cited

U.S. PATENT DOCUMENTS

| | | | |
|---|---|---|---|
| 3,053,277 | 9/1962 | Bahrani | 137/606 |
| 4,078,576 | 3/1978 | Punch et al. | 137/606 |
| 4,163,523 | 8/1979 | Vincent | 137/860 |
| 4,604,093 | 8/1986 | Brown et al. | 137/625.11 |
| 4,605,396 | 8/1986 | Tseo et al | 604/32 |
| 5,033,714 | 7/1991 | Winchell et al. | 604/246 |
| 5,055,003 | 10/1991 | Svensson | 137/860 |
| 5,190,524 | 3/1993 | Wex | 604/80 |
| 5,207,641 | 5/1993 | Allton | 604/32 |
| 5,279,330 | 1/1994 | Debush | 137/860 |
| 5,441,080 | 8/1995 | Baumann | 137/625.44 |

FOREIGN PATENT DOCUMENTS

| | | | |
|---|---|---|---|
| 6-137442 | 5/1994 | Japan | 137/625 |

Primary Examiner—Mark Bockelman
Assistant Examiner—Ronald K. Stright, Jr.
Attorney, Agent, or Firm—Banner & Witcoff, LTD.

[57] ABSTRACT

Safety connector for infusion therapy for supplying several lines and having a casing (1) in which there is a chamber (4) that is bordered by an essentially cylindrical inside wall (5) of the casing into which several connecting channels (2) for joining infusion lines open and which has an outlet channel (9) for attaching an outlet line. The cylindrical outside wall of an elastic ring-shaped valve body is in contact with the inside wall (5) of casing (1) that surrounds chamber (4). The safety connector is simple and inexpensive and has an uncomplicated design. The cylindrical contact surfaces between the ring-shaped valve body and the cylindrical inside wall (5) surrounding chamber (4) result in a good seal for the non-return valves even at a low contact pressure. The sealing force can be determined even down to a very low pressure. Thus, for the first time a safety connector suitable for gravity infusion systems is available.

11 Claims, 1 Drawing Sheet

SAFETY CONNECTOR FOR INFUSION THERAPY

This invention concerns a safety connector of the type characterized in the generic portion of claim 1 for infusion therapy for connecting several infusion lines.

German Patent 4,004,134 A1 discloses a safety connector of the type in question here. It has a casing through which the infusion fluid flows with several passages that can be closed separately and with an outlet for the combined fluid. The passages are bent at an angle and open into a common plane. An elastic sealing element that is essentially angular in cross-section is held with one leg essentially at right angles to the aforementioned plane and with the other leg pressing against the openings to the passages with a spring pressure in the aforementioned plane, thus sealing them. This forms a type of non-return valve for each passage that prevents injection fluid out of one passage from entering the orifice of another passage.

This known safety connector suffers from several disadvantages. First, it has an extremely complicated design. The sealing element which has an angular cross-section must be positioned accurately and with a sealing effect. In addition, it must come in close contact with the surface of the orifice with its sealing leg in the plane where the passages open. Since the contact force is generated here by a pivoting movement of the sealing leg of the sealing element, it is extremely difficult not only to achieve a complete seal around the orifice area of a passage but also to achieve this for all passages. Furthermore, this can be the case only if the contact force is relatively high. But then the opening pressure must also be relatively high. For this reason, this known safety connector is not suitable for gravity infusion systems.

German Utility Patent 7,422,657 discloses a multiple connector for lines for medical equipment with an inside cone at the side for attaching a connecting piece with an outside cone and an elastic length of tubing that is arranged in the area of the connecting piece at the side and in the normal state is in contact with the inside wall of the multiple connector. The inside cone has a diameter such that when inserted in position, the face of the outside cone of the connector forces the length of tubing out of its sealing position into the open position. The length of elastic tubing could also function as a non-return valve and should open temporarily when a high enough injection pressure is created with the help of an injection syringe. Supplying an injection solution presupposes that a high enough pressure can be produced in the injection line. Thus, the use range of this known connector is greatly limited and in any case it is not suitable for gravity infusion equipment. If the connector is also designed as a multiple connector, it must have a complicated design, where several connections for several different infusion lines are provided on a long central length of tubing. This yields a long and complicated design.

This invention is based on the problem of creating a safety connector of the type characterized in the generic portion of claim 1 for infusion therapy for joining several infusion lines, such that it has a simple design and is inexpensive to manufacture, easy to operate and is especially suitable for use with gravity infusion systems.

The problem on which this invention is based is solved by the teaching given in the characterizing part of claim 1.

The basic idea of this invention consists of arranging excess pressure valves for the individual connecting channels in a cylindrical surface. Such a cylindrical surface can essentially be manufactured easily and accurately. For this purpose, the chamber provided between the connecting channels and the outlet channel is bordered by an essentially cylindrical inside wall of the casing. The connecting lines open into this cylindrical inside wall of the casing. The elastic valve body is designed with a ring shape and has a cylindrical outside wall that is in contact with the inside wall of the casing that surrounds the chamber in which the connecting channels also open. Both the aforementioned inside wall of the casing as well as the cylindrical outside wall of the ring-shaped valve body can be manufactured with a high precision, so a leakproof seal of the resulting non-return valves is assured even with a very low contact pressure. At the same time the contact pressure can be determined with a high degree of accuracy from the circumference of the ring-shaped valve body with respect to the circumference of the cylindrical inside wall of the casing. In addition, the contact force is determined by the elastic yield of the ring-shaped body in the circumferential direction. Thus, the entire circumferential length of the ring-shaped valve body enters into the contact force, and since the latter can be determined with a high degree of accuracy, the contact force and thus also the sealing force can be determined with a high degree of accuracy. This is especially also true of very low pressures down to just a few centimeters of a column of water, so the safety connector according to this invention is especially suitable for joining several gravity infusion lines due to the design of the valves.

According to another embodiment of this invention, the axial extent of the cylindrical wall of the valve body is smaller than the axial extent of the cylindrical inside wall of the casing. This assures free mobility of the valve body which is especially important at low opening pressures.

In this embodiment, it is expedient for the casing to have projections that extend into the chamber and hold the ring-shaped valve body in its axial position. These projections are preferably arranged and designed in such a way that a space for passage of the infusion fluid is formed at the axial edges of the ring-shaped valve body.

The casing is preferably disk-shaped and the outlet channel is arranged axially, preferably coaxially with the casing. This yields a simple axially symmetrical exterior that is advantageous especially when there is a connecting channel running axially with respect to the outlet channel according to another embodiment of this invention, where this connecting channel is suitable for joining several safety connectors according to this invention, but it can also be used as a vent line.

Another embodiment of this invention consists of the fact that the chamber is ring-shaped. Therefore, the collecting space between the individual connecting channels and the outlet channel is very small, so there is no unused dead space that could lead to the problematical situation where infusion fluid collects there and is not conveyed further until a different type of infusion fluid is supplied and thus its effect is delayed.

The ring-shaped valve body is preferably in the shape of a short length of tubing. Thus, it can easily be produced by simply cutting short pieces of elastic to size. It is also advantageous that the inside wall of the length of tubing has a crowned cross-section. As a result, the elastic flexibility of the cylindrical valve body increases at the edges, but on the other hand it is also greater in the direction of neighboring orifices of connecting channels. This greatly reduces the danger of transfer of infusion fluids from the orifice of one inlet channel into the orifice of another inlet channel.

Another embodiment of this invention serves the same goal, where recesses that communicate with the chamber are arranged between the orifices of the connecting channels in the cylindrical inside wall of the casing which surrounds the chamber. As a result, infusion liquid trying to flow from one orifice of a connecting channel in the direction of the orifice of another connecting channel must necessarily enter these recesses and thus also the central collecting chamber. In other words, the recesses effectively result in a separation of the individual low-pressure valves from each other. The recesses are preferably in the shape of axial bore holes extending beyond the axial edges of the cylindrical outside wall of the ring-shaped valve body.

In the teaching according to this invention, the cylindrical inside wall of the casing bordering the chamber should be essentially cylindrical. This means of course that deviations with which those skilled in the art are familiar and that take into account the nature of this invention are also possible. Thus, for example, the inside wall may also have a slightly conical form or it may also have a crowned shape. Such a crown shape is more difficult to produce, but it leads, for example, to the same advantage as the crown in the inside surface of the valve body formed essentially by the length of tubing. This crown shape increases the contact force in the central area of the orifice of the connecting channel, so this prevents an exchange of infusion fluid between the connecting channels and thus promotes the flow toward the edges of the valve body and therefore into the chamber.

Figure 3:
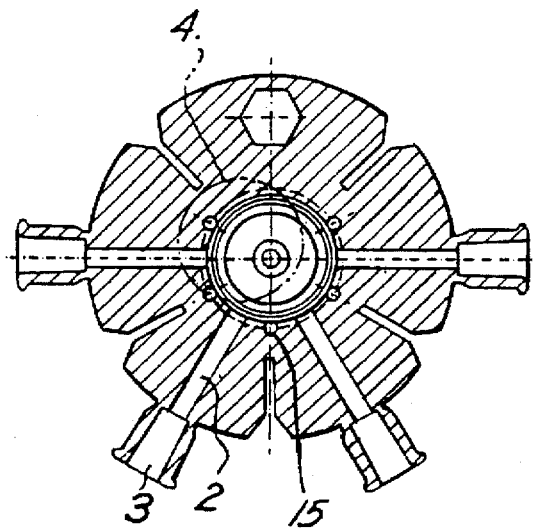
Figure 2:
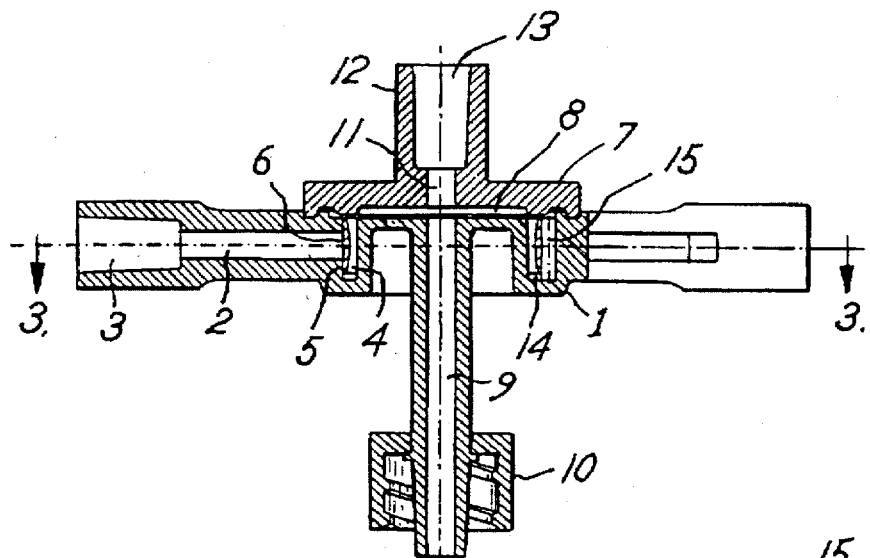
Figure 4:
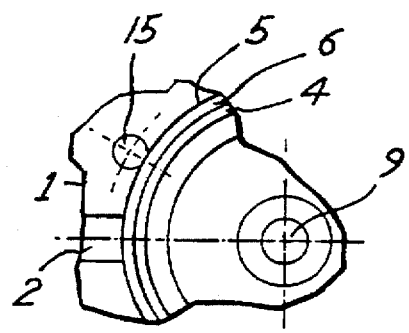

This invention will be illustrated in greater detail on the basis of one example with reference to the figures which show the following:

FIG. 1 shows a top view of an embodiment of a safety connector according to this invention, FIG. 2 shows a section II—II through FIG. 1, FIG. 3 shows an enlarged section III—III through FIG. 2 and FIG. 4 shows an enlarged detail IV from FIG. 3.

As shown by FIGS. 1 to 3, the safety connector according to this invention has an essentially disk-shaped casing 1 which contains connecting channels 2 that are arranged radially or in a star pattern and continue outward in Luer-Lok connections 3 and open on the inside into a ring-shaped chamber 4 that is bordered on the outside by a cylindrical inside wall 5 of casing 1 against which a valve body in the form of a short length of tubing 6 with a cylindrical outside surface is in close contact with a given contact force that is usually very low.

Ring-shaped chamber 4 is sealed off by a disk-shaped housing part 7 that is cemented to casing 1. Ring-shaped chamber 4 communicates with an outlet line 9 through a narrow disk-shaped space 8 and there is a connecting piece 10 at the end of this outlet line. In addition, the disk-shaped space 8 communicates with a connecting channel 11 which is in turn connected to a connecting piece 12 that has an inside cone 13 with the help of which another safety connector of the same type can be connected, thus multiplying the possible number of infusion lines. The connecting piece 12 may also simply be sealed off and opened only for the purpose of venting.

As shown in FIG. 2, the inside surface of the short length of tubing 6 which forms the valve body is designed with a crown-shaped spherically turned cross-section. Therefore, the contact force in the middle area is greater than that at the edges. When there is an excess pressure, the infusion fluid thus escapes mainly over the edges into chamber 4, so this reduces the danger that infusion fluid from one orifice of one of the connecting channels 2 can enter the orifice of a neighboring connecting channel 2.

As also shown in FIG. 2, casing 1 has projections 14 extending toward the ring-shaped chamber 4 so they are in contact with the edges of the short length of tubing 6. These projections hold the short length of tubing 6 in an aligned position with respect to the orifices of the connecting channels 2.

Also, as seen in FIG. 2, the line III—III may be considered an axis through the casing 1. The axial extent of the cylindrical outside wall of the valve body 6 is less than the axial extent of the cylindrical inside wall of the casing 1, thus accommodating movement of the valve body 6 with the casing 1 and assuring free mobility of the ring-shaped valve body.

As shown in FIG. 3 and especially the enlarged detail IV from FIG. 3 in FIG. 4, recesses 15 that extend beyond the edges of the short length of tubing 6 are provided between the orifices of neighboring connecting channels in the cylindrical inside wall of casing 1, as shown in FIG. 2. This creates an outward flow between the orifices of the connecting channels 2 so that infusion fluid can flow through this outlet into chamber 4 after penetrating through the sealed area between the inside wall 5 of the casing 1 and the outside wall of the short length of tubing 6 in the direction of a neighboring orifice of a connecting channel 2. Therefore, such penetrating fluid cannot reach the orifice of the next connecting channel and penetrate into it. This prevents unwanted mixing of infusion fluids due to back flow into another infusion line.

In summary, infusion fluid can flow into the casing 1 through one or more of the Luer-Lok connections 3 into the associated connecting channels 2. Infusion fluid will flow past the ring-like valve body 6 which includes a short length of tubing associated with each connecting channel 2, into chamber 4, then into chamber 8 and then into the outlet line, which connects to a line that communicates to a patient. The valve body 6 will close against the end of the associated connecting channel 2 when pressure increases sufficiently in the chamber 4 to overcome the pressure in the associated connecting channel and thus prevent infusion fluid from a second connecting channel from entering the associated connecting channel 2.

We claim:

1. A safety connector for infusion therapy for supplying several infusion lines having a casing, and a chamber arranged in the casing so that several connecting channels for connecting infusion lines open into this chamber and the chamber has an outlet channel for connection of an outlet line, and with an elastic valve body arranged in the chamber so that it seals the orifices of the connecting channels with a wall that extends over all the orifices of the connecting channels such that non-return valves for all the connecting channels are formed by (a joint) said valve body, the improvement comprising, the chamber (4) is bordered by an essentially cylindrical inside wall (5) of the casing (1), the connecting channels (2) open into the cylindrical wall (5) of the casing (1), the elastic valve body is ring-shaped and has a cylindrical outside wall, the elastic valve body covering the orifices and allowing fluid flow therethrough in one direction, but preventing return flow; and the cylindrical outside wall of the valve body is in contact with the cylindrical inside wall (5) of the casing (1) that surrounds chamber (4)

wherein infusion fluid will flow into the chamber when the pressure in a connecting channel is higher than that in the chamber, and the elastic valve body will prevent the flow of infusion fluid into said connecting channel when the pressure in the chamber is higher than that in said connecting channel.

2. A safety connector according to claim 1, characterized in that the axial extent of the cylindrical outside wall of the valve body is smaller than the axial extent of the cylindrical inside wall (5) of casing (1).

3. A safety connector according to claim 2, characterized in that the casing (1) has projections (14) extending into chamber (4) to hold the ring-shaped valve body in its axial position.

4. A safety connector according to claim 3, characterized in that the projections (14) are arranged and designed in such a way that a space for passage of infusion fluid is formed at the axial edges of the ring-shaped valve body.

5. A safety connector according to claim 1, characterized in that the casing (1) is disk-shaped and the outlet channel (9) is arranged axially or preferably coaxially with it.

6. A safety connector according to claim 5, characterized in that a connecting channel (11) is arranged axially with respect to the outlet channel (9).

7. A safety connector according to claim 1, characterized in that the ring-shaped valve body is in the shape of short length tubing (6).

8. A safety connector according to claim 7, characterized in that the inside wall of the short length of tubing (6) has a crown-shaped cross-section.

9. A safety connector according to claim 1, characterized in that the casing is provided with recesses that communicate with chamber (4), said recesses being (are) arranged between the orifices of the connecting channels (2) in the inside wall (5) of the casing (1) surrounding the chamber (4).

10. A safety connector according to claim 9, characterized in that the recesses are in the form of axial bore holes (15) that extend beyond the axial edges of the cylindrical outside wall of the ring-shaped valve body.

11. A safety connector according to claim 1, characterized in that chamber (4) is ring-shaped.

* * * * *